United States Patent
Laura Lapoint et al.

(10) Patent No.: US 9,463,294 B2
(45) Date of Patent: Oct. 11, 2016

(54) SYSTEM AND METHOD OF PROVIDING FEEDBACK TO A SUBJECT RECEIVING RESPIRATORY THERAPY VIA A CLIENT DEVICE ASSOCIATED WITH THE SUBJECT

(75) Inventors: Manuel Laura Lapoint, Pittsburgh, PA (US); Nathan Francis O'Connor, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 560 days.

(21) Appl. No.: 13/995,189

(22) PCT Filed: Dec. 13, 2011

(86) PCT No.: PCT/IB2011/055640
§ 371 (c)(1),
(2), (4) Date: Jun. 18, 2013

(87) PCT Pub. No.: WO2012/085756
PCT Pub. Date: Jun. 28, 2012

(65) Prior Publication Data
US 2013/0269700 A1    Oct. 17, 2013

Related U.S. Application Data

(60) Provisional application No. 61/424,886, filed on Dec. 20, 2010.

(51) Int. Cl.
*A61M 11/00* (2006.01)
*A61M 16/00* (2006.01)
(Continued)

(52) U.S. Cl.
CPC ........ *A61M 16/0057* (2013.01); *A61B 5/0022* (2013.01); *A61B 5/08* (2013.01);
(Continued)

(58) Field of Classification Search
CPC ........... A61M 16/00; A61M 16/0003; A61M 2016/0027; A61M 16/0051; A61M 16/0057; A61M 16/0666; A61M 16/0434; A61M 16/0875; A61M 16/12; A61M 16/0066; A61M 2230/432; A61M 2205/3584; A61M 16/0075; A61M 2205/356; A61B 5/08; A61B 5/0022; A61B 5/4833; A61B 5/0836; A61B 5/087; A61B 5/486
USPC .......................... 128/204.18, 204.21, 204.23
See application file for complete search history.

(56) References Cited

U.S. PATENT DOCUMENTS 5,363,842 A * 11/1994 Mishelevich ........ A61B 8/0875
128/200.14
5,517,983 A * 5/1996 Deighan ............... A61M 16/00
128/204.21
(Continued)

FOREIGN PATENT DOCUMENTS

EP         1900387 A1    3/2008
JP      2003531663 A    10/2003
(Continued)

*Primary Examiner* — Steven Douglas

(57) ABSTRACT

Feedback information is provided to a subject regarding reception of pressure support therapy, and/or other respiratory support therapy. The feedback information may indicate compliance to a respiratory therapy regimen. The feedback information is provided to the subject by transmitting the feedback information through a communication network to a client device associated with the subject. The feedback information may include a characterization of the therapy received by the subject with respect to a usage goal.

15 Claims, 4 Drawing Sheets

(51) Int. Cl.
  A61B 5/00      (2006.01)
  A61B 5/08      (2006.01)
  A61M 16/04     (2006.01)
  A61M 16/06     (2006.01)
  A61M 16/08     (2006.01)
  A61M 16/12     (2006.01)
  A61B 5/083     (2006.01)
  A61B 5/087     (2006.01)

(52) U.S. Cl.
  CPC ....... *A61B 5/4833* (2013.01); *A61M 16/0051* (2013.01); *A61M 16/0434* (2013.01); *A61M 16/0666* (2013.01); *A61M 16/0875* (2013.01); *A61M 16/12* (2013.01); *A61B 5/087* (2013.01); *A61B 5/0836* (2013.01); *A61B 5/486* (2013.01); *A61M 16/0066* (2013.01); *A61M 16/0072* (2013.01); *A61M 16/0075* (2013.01); *A61M 2016/0027* (2013.01); *A61M 2016/0033* (2013.01); *A61M 2205/3561* (2013.01); *A61M 2205/3584* (2013.01); *A61M 2230/432* (2013.01)

(56) References Cited

U.S. PATENT DOCUMENTS

| | | | |
|---|---|---|---|
| 6,135,106 A * | 10/2000 | Dirks | A61M 16/00 128/204.18 |
| 6,910,481 B2 * | 6/2005 | Kimmel | A61M 16/0051 128/202.22 |
| 7,225,809 B1 * | 6/2007 | Bowen | A61M 16/00 128/204.18 |
| 7,591,265 B2 * | 9/2009 | Lee | A61M 16/00 128/204.18 |
| 7,913,689 B2 * | 3/2011 | Henry | A61M 16/00 128/204.18 |
| 2005/0061315 A1 | 3/2005 | Lee et al. | |
| 2005/0188991 A1 | 9/2005 | Sun et al. | |
| 2008/0319797 A1 | 12/2008 | Egami et al. | |
| 2009/0229610 A1 | 9/2009 | Oates et al. | |
| 2010/0019910 A1 | 1/2010 | Hassing et al. | |
| 2010/0049008 A1 | 2/2010 | Doherty et al. | |
| 2010/0078017 A1 * | 4/2010 | Andrieux | A61M 16/209 128/202.22 |
| 2010/0199102 A1 | 8/2010 | Knepper et al. | |

FOREIGN PATENT DOCUMENTS

| | | |
|---|---|---|
| JP | 2009518731 A | 5/2009 |
| WO | 0182789 A2 | 11/2001 |
| WO | 2007075588 A2 | 7/2007 |
| WO | 2009036327 A1 | 3/2009 |
| WO | 2010116275 A1 | 10/2010 |

* cited by examiner

Congratulations, you hit your goal!

Last night's AHI: 0.5
Last night's goal: 3.0 hrs
Last night's usage: 6.0 hrs

Tomorrows goal: 3.5 hrs

FIG. 3

Using CPAP can be difficult at first.
Be sure to contact your provider if
you having difficulties.

Last night's AHI: 1.0
Last night's goal: 3.0 hrs
Last night's usage: 2.0 hrs

Tomorrows goal: 2.5 hrs

FIG. 4

SYSTEM AND METHOD OF PROVIDING FEEDBACK TO A SUBJECT RECEIVING RESPIRATORY THERAPY VIA A CLIENT DEVICE ASSOCIATED WITH THE SUBJECT

The invention relates to providing usage reports with feedback information to a subject receiving respiratory therapy to encourage compliance with a respiratory therapy regimen.

Systems for providing positive airway pressure therapy to subjects are known. These systems generate a pressurized flow of breathable gas that is provided to the airway of a subject during sleep to support the subject's airway. The support provided by the pressurized flow of breathable gas to the airway of the subject enables the subject to avoid sleep disordered breathing.

Generally, reception of a pressurized flow of breathable gas at the airway is considered uncomfortable by subjects. Conventional systems may also be inconvenient for subjects who travel and have to transport a system to in order to receive positive airway pressure therapy. Other obstacles to usage of conventional systems also exist. Consequently, compliance of subjects to positive airway pressure support regimes may be less than optimal.

One aspect of the disclosure relates to a system configured to provide feedback to a subject regarding compliance to a respiratory therapy regimen. In one embodiment, the system comprises one or more processors configured to execute computer program modules including a usage module and a feedback module. The usage module is configured to monitor usage of a pressure support device configured to deliver a pressurized flow of breathable gas to the airway of the subject in accordance with the therapy regimen. Usage of the pressure support device by the subject includes receiving the pressurized flow of breathable gas into the airway. The feedback module is configured to provide to the subject feedback information related to the usage of the pressure support device by the subject, wherein the feedback module is configured to transmit the feedback information to a client device associated with the subject through a communication network.

Another aspect of the disclosure relates to a method of providing feedback to a subject regarding compliance to a respiratory therapy regimen. In one embodiment, the method comprises monitoring usage of a pressure support device configured to deliver a pressurized flow of breathable gas to the airway of the subject in accordance with the therapy regimen, wherein usage of the pressure support device by the subject includes receiving the pressurized flow of breathable gas into the airway; and transmitting, through a communication network to a client device associated with the subject, feedback information related to usage of the pressure support device by the subject.

Yet another aspect of the disclosure relates to a system for providing feedback to a subject regarding compliance to a respiratory therapy regimen. In one embodiment, the system comprises means for monitoring usage of a pressure support device configured to deliver a pressurized flow of breathable gas to the airway of the subject in accordance with the therapy regimen, wherein usage of the pressure support device by the subject includes receiving the pressurized flow of breathable gas into the airway; and means for transmitting, through a communication network to a client device associated with the subject, feedback information related to usage of the pressure support device by the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not a limitation. In addition, it should be appreciated that structural features shown or described in any one embodiment herein can be used in other embodiments as well. It is to be expressly understood, however, that the drawings are for the purpose of illustration and description only and are not intended as a definition of limits. As used in the specification and in the claims, the singular form of "a", "an", and "the" include plural referents unless the context clearly dictates otherwise.

FIG. 3 illustrates a usage report provided to a subject via a client device associated with the subject.

FIG. 4 illustrates a usage report provided to a subject via a client device associated with the subject.

Figure 1:
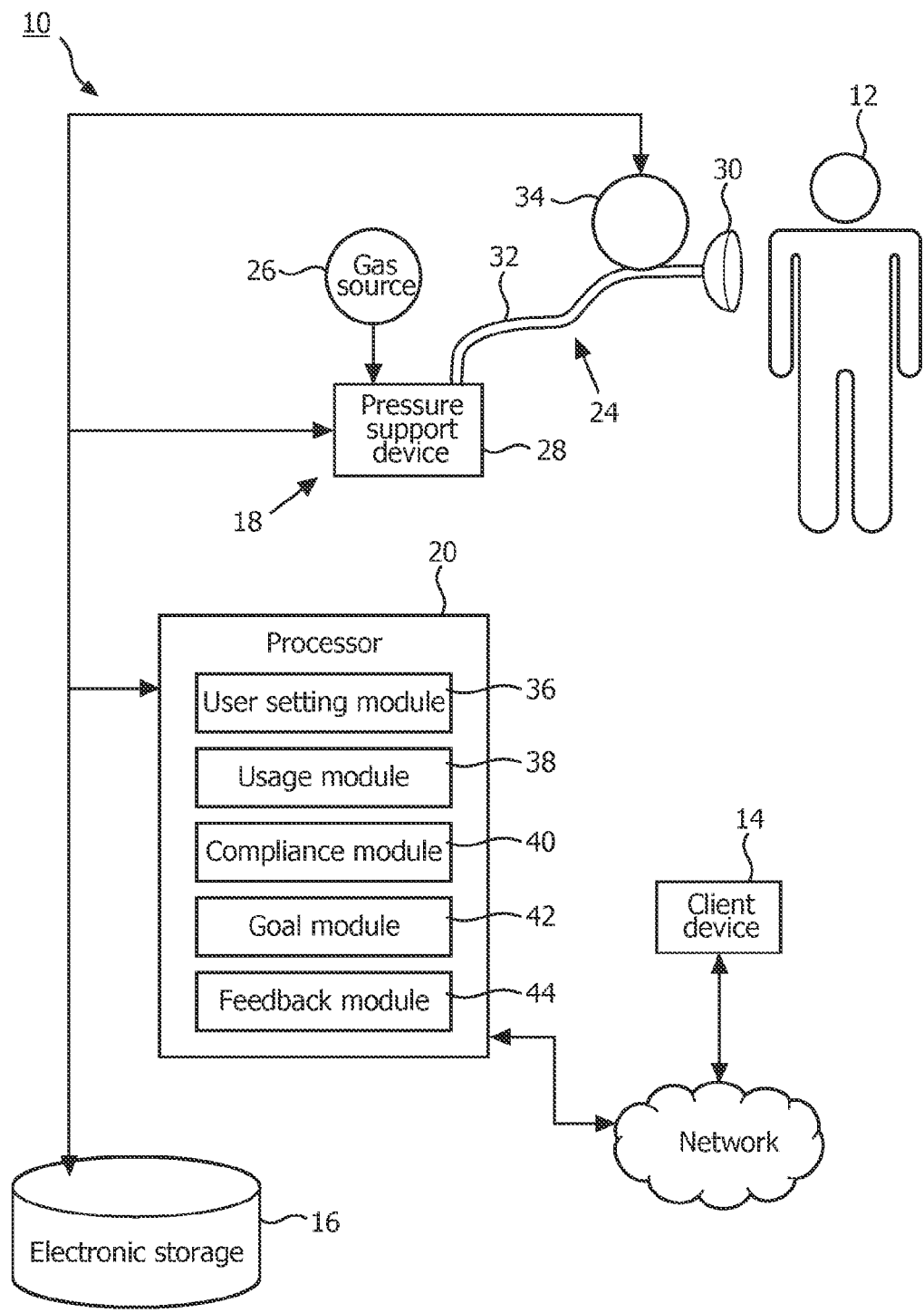
FIG. 1 illustrates a system configured to provide feedback information to a subject regarding reception of therapy.

FIG. 1 illustrates a system 10 configured to provide feedback information to a subject 12 regarding reception of pressure support therapy, and/or other respiratory support therapy. The feedback information may indicate compliance to a respiratory therapy regimen. The feedback information is provided to the subject by system 10 to subject 12 through a client device 14 associated with subject 12. The feedback information may include a characterization of the therapy received by subject 12 with respect to a usage goal. Although specific mention is made herein to respiratory therapies such as pressure support therapy, it will be appreciated that this is not intended to be limiting. The principles described herein with respect to system 10 extend to encouraging compliance with any type of therapy regimen. In one embodiment, system 10 includes electronic storage 16, a pressure generator 18, a processor 20, and/or other components.

The client device 14 is a client computing platform having one or more processors configured to execute computer program modules, a user interface including a control input and an electronic display, and/or other components. The client device 14 is configured to receive communication through a communication network, such as the Internet, a wireless communication network, and/or other communication networks. The client device 14 may be configured to receive information through the communication network wirelessly and/or through wired communication media. As non-limiting examples, the client device 14 may include one or more of a desktop computer, a laptop computer, a handheld computer, a personal digital assistant, a mobile telephone, a smartphone, and/or other client computing platforms. The computer program modules executed by client device 14 may be associated with a client application that enables client device 14 to communicate with the rest of system 10 through the communication network, and to configure interfaces for presentation to subject 12 on client device 14. For example, the client application may include one or more of an email client, a web browser, an SMS client, an MMS client, a dedicated client application (or "app"), and/or other client applications. Through the interface presented to subject 12 on client device 14, the client application may be configured to receive entry and/or selection of control inputs by subject 12.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, computer program modules, information determined by processor 20, information received via user interface 16, and/or other information that enables system 10 to function properly. Electronic storage 16 may be a separate component within system 10, or electronic storage 16 may be provided integrally with one or more other components of system 10. Although electronic storage 16 is illustrated in FIG. 1 as a single entity, in one embodiment, electronic storage 16 includes a plurality of electronic media divided amongst a plurality of different devices and/or components within system 10.

Pressure generator 18 is configured to generate a pressurized flow of breathable gas for delivery to the airway of subject 12 by a circuit 24. One or more parameters of the pressurized flow of breathable gas generated by pressure generator 18 may be controlled in accordance with a pressure therapy algorithm designed to provide positive airway pressure support to subject 12 during bedtime, and/or to provide other types of respiratory therapy to subject 12. The pressure therapy algorithm may include one or more of a bi-PAP algorithm, a CPAP algorithm, auto-titrating CPAP, servo-ventilation, backup breaths, comfort features such as C-Flex, reducing pressure during early exhalation, and/or other pressure therapy algorithms. The one or more parameters of the pressurized flow of breathable gas controlled in accordance with the pressure therapy algorithm may include one or more of a pressure, a flow rate, a composition, a volume, and/or other parameters of the pressurized flow of breathable gas. In one embodiment, pressure generator 18 includes a gas source 26 and a pressure support device 28.

Gas source 26 includes a body or bodies of gas from which pressure support device 28 generates the pressurized flow of breathable gas that is delivered to subject 12. Gas source 26 may include any supply of breathing gas, such as, for example, ambient atmosphere, a tank of pressurized gas, a wall gas source, and/or other bodies of breathable gas. The breathing gas from gas source 26 can be any breathable gas, such as air, oxygen, an oxygen mixture, a mixture of a breathing gas and a medication, which can be in gaseous form (e.g., nitric oxide, nebulized, etc.), and/or other breathable gases.

Pressure support device 28 includes one or more mechanisms for controlling one or more parameters of the flow of breathable gas released from pressure support device 28 to circuit 24 (e.g., pressure, flow, etc.). For example, pressure support device 28 may include one or more of a valve, a blower, a piston, a bellows, and/or other mechanisms for controlling one or more parameters of the flow of breathable gas.

Circuit 24 defines a gas flow path between pressure generator 18 and the airway of subject 12. As such, circuit 24 is configured to deliver the pressurized flow of gas from pressure generator 18 to the airway of subject 12. In one embodiment, circuit 24 includes one or more of an interface appliance 30 and a conduit 32.

Interface appliance 30 is configured to provide gas to and receive gas from the airway of subject 12. Interface appliance 30 may include may include either an invasive or non-invasive appliance for communicating gas between circuit 24 and the airway of subject 12. For example, interface appliance 30 may include a nasal mask, nasal/oral mask, total face mask, nasal cannula, endotracheal tube, LMA, tracheal tube, and/or other interface appliance.

Conduit 32 forms a flow path between pressure support device 18 and interface appliance 30. In one embodiment, conduit 32 is flexible.

Although circuit 24 is illustrated in FIG. 1 as a single-limbed circuit for communicating a pressurized flow of breathable gas with the airway of subject 12, this is not intended to be limiting. In one embodiment circuit 24 is a double-limbed circuit with a separate portion configured to convey gas away from the airway of subject 12.

In one embodiment, system 10 includes one or more sensors 34. The sensors 34 are configured to monitor one or more parameters of the pressurized flow of breathable gas delivered to the airway of subject 12. For example, sensors 34 may include one or more sensors configured to generate output signals conveying information related to one or more a pressure, a flow rate, a composition, a volume, and/or other parameters of the pressurized flow of breathable gas. Such sensors may include, for instance, one or more of a pressure sensor, a flowmeter, a capnometer, and/or other sensors configured to generate output signals conveying information related to one or more parameters of the pressurized flow of breathable gas. The sensors 34 may be disposed in system 10 so as to be in communication with the pressurized flow of breathable gas inside pressure support device 28, inside circuit 24, and/or at or near the airway of subject 12. For example, one or more of sensors 34 may be disposed in a positive airway pressure support system that includes pressure support device 28, interface appliance 30, and/or conduit 32.

In one embodiment, pressure support device 28 is the base unit of system 10, and includes a housing with a port to which conduit 32 is removably coupled. The pressure support device 28 further includes a user interface carried on the housing that enables subject 12 and/or other users to control therapy provided to subject 12, turn pressure support device 28 on and/or off, receive feedback about the therapy provided by pressure support device 28, and/or otherwise communicate information between subject 12 and pressure support device. For example, the user interface carried on pressure support device 28 may include a screen, a speaker, a button, a switch, a knob, an indicator light, and/or other interface devices. The housing of pressure support device 28 may carry electronic storage media and/or information processing components providing some or all of the functionality attributed to electronic storage 16 and/or processor 20.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 16 is shown in FIG. 1 as a single entity, this is for illustrative purposes only. In some implementations, processor 16 may include a plurality of processing units. These processing units may be physically located within the same device, or processor 16 may represent processing functionality of a plurality of devices operating in coordination. For example, in one embodiment, the functionality attributed below to processor 16 is divided between a first processor (or processors) that is included in the housing of pressure support device 28 and a second processor (or processors) that are included in a server located remotely from pressure support device 28. The first processor and second processor may communicate (e.g., via a communication network) to provide the functionality attributed herein to processor 20. The server may be configured to support a plurality of pressure support devices like pressure support device 28 in a centralized manner.

As is shown in FIG. 1, processor 20 may be configured to execute one or more computer program modules. The one or more computer program modules may include one or more of a user setting module 36, a usage module 38, a compliance module 40, a goal module 42, a feedback module 44, and/or other modules. Processor 20 may be configured to execute modules 36, 38, 40, 42, and/or 44 by software; hardware; firmware; some combination of software, hardware, and/or firmware; and/or other mechanisms for configuring processing capabilities on processor 20.

It should be appreciated that although modules 36, 38, 40, 42, and 44 are illustrated in FIG. 1 as being co-located within a single processing unit, in implementations in which processor 20 includes multiple processing units, one or more of modules 36, 38, 40, 42, and/or 44 may be located remotely from the other modules. For example, one or more of modules 36, 38, 40, 42, and/or 44 may be located in a server that is remote from pressure support device 28. The description of the functionality provided by the different modules 36, 38, 40, 42, and/or 44 described below is for illustrative purposes, and is not intended to be limiting, as any of modules 36, 38, 40, 42, and/or 44 may provide more or less functionality than is described. For example, one or more of modules 36, 38, 40, 42, and/or 44 may be eliminated, and some or all of its functionality may be provided by other ones of modules 36, 38, 40, 42, and/or 44. As another example, processor 20 may be configured to execute one or more additional modules that may perform some or all of the functionality attributed below to one of modules 36, 38, 40, 42, and/or 44.

The user setting module 36 is configured to manage settings configured by subject 12 and/or other users (e.g., a caregiver, a therapy decision-maker, a researcher, and/or other users) regarding the therapy received by subject 12. The settings may include one or more settings related to a usage goal, a destination for communications from system 10 transmitted to client device 14 (e.g., a device ID, a MAC address, an email address, a phone number, and/or other destination identifications), a username and/or login, and/or other settings. Selection and/or entry of configuration of the settings from the user(s) may be received via the user interface carried by the housing of the pressure support device 28, via client device 14, via another client device (e.g., associated with a caregiver, a therapy decision-maker, a researcher, and/or other users), and/or through other user interfaces.

The usage module 38 is configured to monitor usage of pressure generator 18 by subject 12. As will be appreciated, the therapeutic benefits of the pressurized flow of breathable gas provided to subject 12 by pressure generator 18 may be enhanced as subject 12 increases the amount of time for which the pressurized flow of breathable gas is received by subject 12. However, subject 12 may find using pressure generator 18 inconvenient, uncomfortable, and/or otherwise troublesome. In monitoring usage of pressure generator 18 by subject 12, usage module 38 quantifies the amount of therapy received by subject 12 from pressure generator 18. For example, the usage of pressure generator 18 by subject 12 may be quantified as the amount of time for which subject 12 receives the pressurized flow of breathable gas from pressure generator 18 via interface appliance 30. Other quantifications of the therapy received by subject 12 from pressure generator 18 may be implemented without departing from the scope of this disclosure.

Usage module 38 monitors usage of pressure generator 18 based on the output signals generated by sensors 34. For example, from the output signals generated by sensors 34, usage module 38 may determined whether or not subject 12 is receiving the pressurized flow of breathable gas from pressure generator 18 at a given time. This includes determining whether interface appliance 30 is installed properly at the airway of subject 12 and determining whether the pressurized flow of breathable gas is currently being generated by pressure generator 18. From this determination, usage module 38 quantifies usage of pressure generator 18 by subject 12 (e.g., by aggregating the time during which subject 12 received the pressurized flow of breathable gas), which provides a measurement of the amount of therapy received by subject 12.

In monitoring usage of pressure generator 18, usage module 38 may quantify usage of pressure generator 18 during individual epoch periods of time and/or during era periods of time that span a plurality of epochs. By way of non-limiting example, epochs may be individual days/nights (e.g., 24 hour periods), and eras may be a predetermined number of days (e.g., a week, 10 days, a month, etc.).

Figure 2:
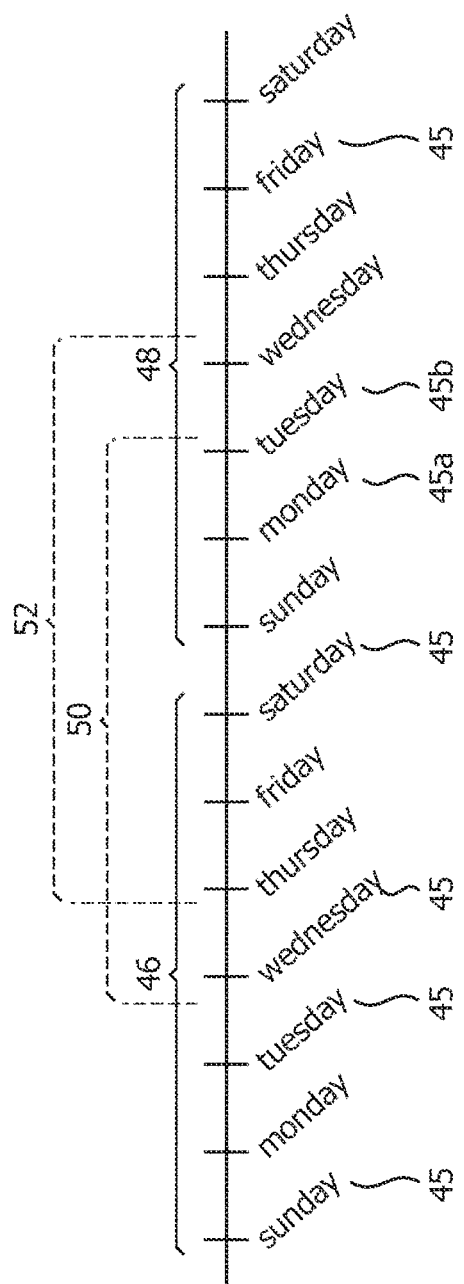
FIG. 2 is a timeline that illustrates the manner in which compliance to a therapy regimen is monitored.

By way of illustration, FIG. 2 depicts the manner in which a module, such as usage module 38 (shown in FIG. 1), monitors usage of a pressure generator by a subject to receive therapy in the form of a pressurized flow of breathable gas delivered to the airway of the user from the pressure generator, according to one embodiment. FIG. 2 includes a timeline that is divided into a plurality of epochs 45. In particular, epochs 45 are individual nights. In the embodiment illustrated in FIG. 2, usage is quantified by the module in terms of the amount of time during a given epoch for which the subject has received the pressurized flow of breathable gas to the airway.

In addition to quantifying usage on a per epoch basis, the module also quantifies usage on a per era basis. In the exemplary embodiment illustrated in FIG. 2, an era is a week (e.g., 7 nights). However, this number of epochs is not intended to be limiting. The module quantifies usage received for a given era by aggregating the usage by the subject during the epochs within the given era. This aggregation may include, for example, adding the amounts of usage, averaging the amounts of usage, determination based on mode, determination of median or mean, discarding outliers (e.g., highest, lowest) prior to aggregating, weighting contributions (e.g., previous day is weighted heaviest while oldest day is weighted least), and/or otherwise aggregating the amounts of usage.

The eras defined by the module may include fixed, non-overlapping periods of time, or an era may be a rolling window of time having a predetermined length. By way of example, FIG. 2 illustrates two consecutive eras 46 and 48 that are fixed in time. Eras 46 and 48 are weeklong periods that span the traditional week (Sunday-Saturday). FIG. 2 further illustrates eras 50 and 52, which would be defined as eras by the module were using a rolling window of time as eras. At the Monday illustrated in FIG. 2 as 45*a*, the current era would be defined by the module as era 50. On the following day, Tuesday 45*b*, the current era is defined by the module as era 52, and so on.

Returning to FIG. 1, in one embodiment, the functionality attributed to usage module is provided by a processor carried within the housing of pressure support device 28. In one embodiment, some or all of the functionality attributed to usage module 38 is provided by a processor located at a server remote from pressure support device 28. In this embodiment, the output signals generated by sensors 34, and/or information derived from the output signals generated by sensors 34, are transmitted from pressure support device 28 to the server. This transmission may occur in real-time, or may occur in an intermittent and/or batched manner (e.g., at the end of a therapy session, on an hourly or daily basis, and/or at other intermittent times). The server may then implement the received output signals and/or information in the manner described above with respect to usage module 38.

The compliance module 40 is configured to monitor compliance of subject 12 in the usage of pressure generator 18. Monitoring compliance of subject 12, in one embodiment, includes characterizing the usage of the pressure support device 28 by subject 12 with respect to a usage goal. This may include determining whether the usage of pressure generator 18 by subject 12 has met or exceeded the usage goal. Characterization of usage with respect to a usage goal by compliance module 40 may be made on an epoch and/or era basis. For example, to monitor compliance on an epoch basis, compliance module 40 compares usage during a given epoch with a usage goal for the given epoch. To monitor compliance on an era basis, compliance module 40 compares usage during a given era with an era goal.

Compliance may be monitored by compliance module 40 for time periods (e.g., epochs, eras, etc.) that have passed and/or for time periods that are currently occurring. For example, in the middle of a given epoch, compliance module 40 determines a characterization of the usage by subject 12 with the usage goal for the given epoch by comparing the current amount of usage by subject 12 in the given epoch with the usage goal for the given epoch. The usage goal may be prorated based on the current time that has passed within the given epoch, or current usage may be compared against the full usage goal even though the given epoch has not yet been concluded.

In one embodiment, the functionality attributed herein to compliance module 40 is provided by a processor carried within the housing of pressure support device 28. In one embodiment, the functionality attributed herein to compliance module 40 is provided, at least in part, by a processor in a server located remotely from pressure support device 28. The remote processor may perform this functionality based on usage information and/or usage goal that are obtained from the pressure support device 28, received from a user, and/or determined on the server. In this embodiment, the remote processor may provide this functionality centrally for a plurality of users that receive therapy from a corresponding plurality of pressure support devices.

Goal module 42 is configured to determine usage goals for implementation by compliance module 38. As is discussed further below, in one embodiment, the goal module 42 determines usage goals dynamically and adaptively to encourage compliance by subject 12. The usage goals may be determined by goal module 42 based on past usage of pressure generator 18 by subject 12. The usage goals determined by goal module 42 may be determined based on received entry and/or selection of usage goals by subject 12 and/or other users. The goals determined by goal module 42 may include epoch usage goals and/or era usage goals. In addition to determining the usage goals, goal module 42 may provide the usage goals to subject 12 in advance so that subject 12 knows what upcoming goals are and/or adjust upcoming goals.

In one embodiment, the functionality attributed herein to goal module 42 is provided by a processor carried within the housing of pressure support device 28. In one embodiment, the functionality attributed herein to goal module 42 is provided, at least in part, by a processor in a server located remotely from pressure support device 28. The remote processor may perform this functionality based on usage information and/or usage goal that are obtained from the pressure support device 28, received from a user, and/or determined on the server. In this embodiment, the remote processor may provide this functionality centrally for a plurality of users that receive therapy from a corresponding plurality of pressure support devices.

Feedback module 44 is configured to provide feedback information to subject 12 in usage reports. The feedback information is related to the usage of the pressure support device by subject 12. The feedback information may include, among other things, a characterization of usage by subject 12 with respect to a usage goal (as determined by compliance module 40), usage information, and/or other information. The feedback information may include textual information, audible information, video information, still images, and/or other types of information. The feedback information may be provided to subject 12 in usage reports.

The feedback module 44 is configured to provide the usage reports to subject 12 by transmitting the feedback information to client device 14 through a communication network. For example, feedback module 44 may be configured to provide the usage reports to client device 14 via one or more of email, short message service message, multimedia messaging service, TCP/IP, a micro-blogging service (e.g., Twitter®), a social network wall post or message (e.g., Facebook®, MySpace™, and/or other social networks), and/or other electronic communications that can be transmitted through a communication network. The transmission of usage reports through TCP/IP may include transmissions from a server performing at least some of the functionality of feedback module 44 to a dedicated client application running on client device 14, transmission of a web page hosted by a server for subject 12 including usage reports, and/or other contexts in which feedback reports are transmitted from a server providing at least some of the functionality of feedback module 44 to client device 14 via TCP/IP.

The feedback module 44 may be configured to include information in the usage reports information and/or content other than just feedback information. Such information may include, for example, messages of encouragement, explanation of the importance of the therapy being provided, tips on usage of the pressure support device 28, messages that convey empathy about the inconvenience, discomfort, or other issues that discourage compliance if subject 12 does not meet the usage goal(s), messages that indicate completion of an epoch goal that provide encouragement to proceed with completion of the overarching era goal, and/or other information. The information included with the usage report may include information related to the impact of the therapy on subject 12. For example, information related to the quality of sleep and/or respiration experienced by subject 12 while receiving therapy may include included in usage reports. Such information may include, for example, an HA index, flow limitation percentage, average apnea length, bed time, sleep time, arousal index, percent improvement from previous night, average leak to indicate whether the patient has a good seal or maybe needs a different mask, sleep stages, and/or other information.

By way of illustration, FIGS. 3 and 4 show exemplary usage reports. As can be seen in FIGS. 3 and 4, the usage reports may include motivational messages, usage information, feedback information, and/or other information. The motivational message provided to a subject may be a function of the characterization of usage with respect to a usage goal. For example, in the usage report of FIG. 3 the subject has exceeded the usage goal and is provided with a first motivational message. In the usage report of FIG. 4 the subject has failed to meet the usage goal and is provided with a second motivational message that is more appropriate for encouraging a user that has failed to meet the usage goal. In the usage reports shown in FIGS. 3 and 4, the feedback information includes characterizations of a subject's usage with respect to a usage goal. In the usage report of FIG. 3, the subject has exceeded the usage goal. In the usage report of FIG. 4, the subject has failed to meet the usage goal. In each of the usage reports shown in FIGS. 3 and 4, a future usage goal is presented to the subject.

Returning to FIG. 1, the feedback module 44 may be configured to transmit usage reports to subject 12 at specific intervals, based on the occurrence of therapy events that trigger a usage report, in response to a request from subject 12 for a usage report, and/or on other intermittent basis. The specific intervals may include periodic intervals. The periodic intervals may coincide with epochs and/or eras corresponding to the usage goals against which usage by subject 12 is being measured. Requests from subject 12 for a usage report may be received by feedback module 44 via a transmission from client device 14 (e.g., a text, an email, a message, a browser request for a web page with a feedback report, and/or other transmissions from client device 14), via selection of a control input on the user interface carried on the housing of pressure support device 28, and/or via other means.

Various parameters of the usage reports transmitted to subject 12 are determined by feedback module 44 based on user settings managed by user settings module 36, and/or based on information included in a request for a usage report. For example, the information in usage reports for subject 12, the type of information (e.g., audio, textual, images, and/or other information types) in usage reports for subject 12, the intervals at which usage reports are generated, the communication media of the usage reports (e.g., email, short message service message, multimedia messaging service, TCP/IP, micro-blogging service, social network wall post or message, etc.), and/or other parameters may be determined by feedback module 44 based on user settings and/or information included in a request for a usage report.

In one embodiment, feedback module 44 is configured to award virtual goods to subject 12 based on usage of the pressure support device 28. Satisfaction of various and/or certain era and/or epoch usage goals may result in virtual goods being awarded to subject 12 within one or more virtual environments. The virtual environments may include, for example, social networks, micro-blogging services, virtual worlds, and/or other virtual environments. The virtual goods may include, for example, digital badges to be displayed and/or worn by an avatar within a virtual environment, virtual clothing, virtual equipment, a virtual gift, an avatar, and/or other virtual goods. A virtual good awarded to subject 12 may be provided to subject 12 in a usage report and/or separate from a usage report.

In one embodiment, the functionality attributed herein to feedback module is provided by a processor carried within the housing of pressure support device 28. In one embodiment, the functionality attributed herein to goal module 42 is provided, at least in part, by a processor in a server located remotely from pressure support device 28. The remote processor may perform this functionality based on usage information and/or usage goal that are obtained from the pressure support device 28, received from a user, and/or determined on the server. In this embodiment, the remote processor may provide this functionality centrally for a plurality of users that receive therapy from a corresponding plurality of pressure support devices.

Figure 5:
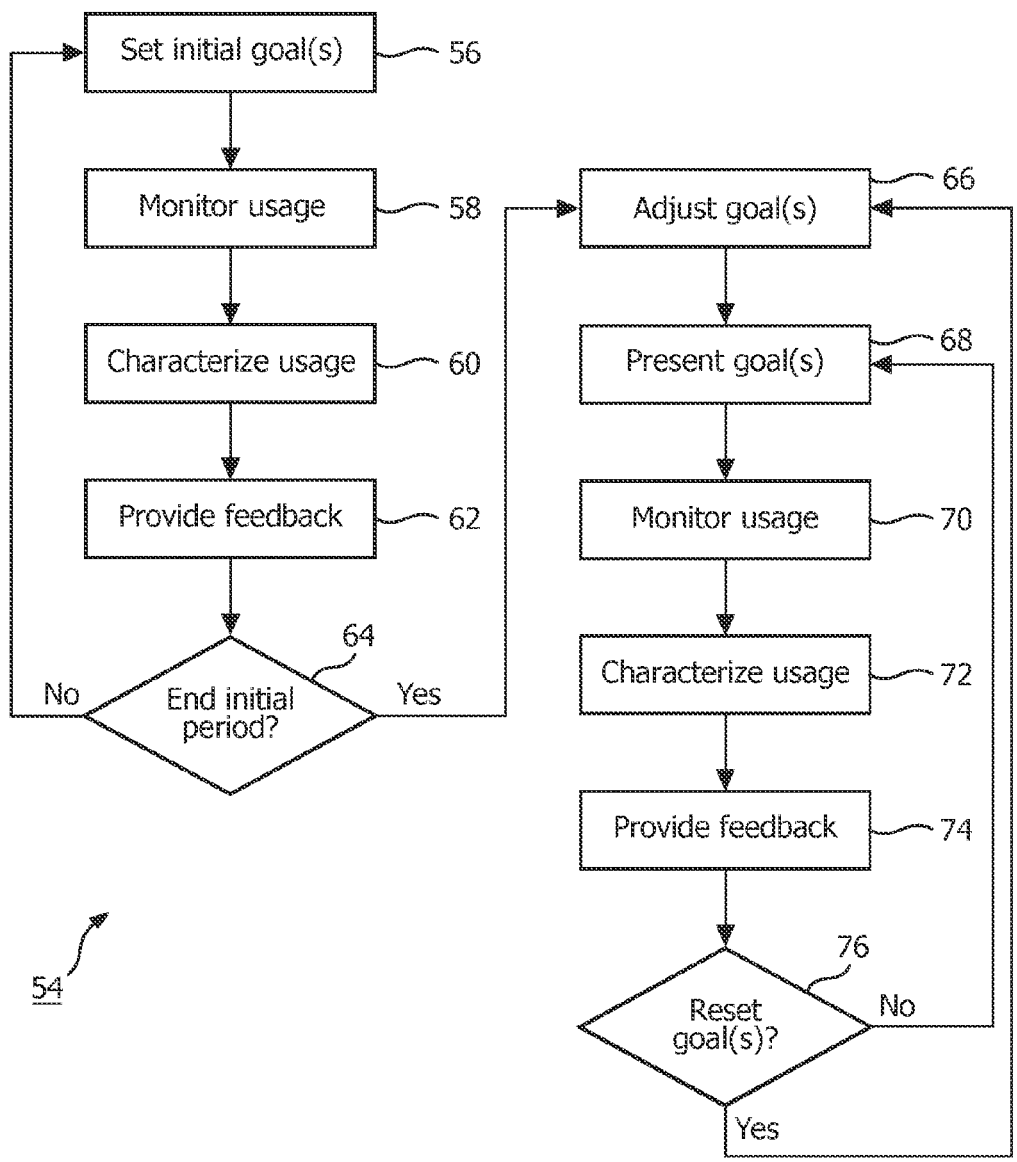
FIG. 5 illustrates a method of reporting usage of a pressure support device to a subject receiving therapy from the pressure support device.

FIG. 5 illustrates a method 54 of reporting usage of a pressure support device to a subject receiving therapy from the pressure support device. The operations of method 54 presented below are intended to be illustrative. In some embodiments, method 54 may be accomplished with one or more additional operations not described, and/or without one or more of the operations discussed. Additionally, the order in which the operations of method 54 are illustrated in FIG. 5 and described below is not intended to be limiting.

In some embodiments, method 54 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 54 in response to instructions stored electronically on an electronic storage medium. The one or more processing devices may include one or more devices configured through hardware, firmware, and/or software to be specifically designed for execution of one or more of the operations of method 54.

At an operation 56, one or more initial usage goals are obtained. In one embodiment, the one or more initial usage goals include an era goal and/or an epoch goal. The initial usage goals identify a goal amount of respiratory therapy that the subject should receive during a corresponding epoch and/or era. The epoch goal corresponds to one or more epochs (e.g., to individual nights). The era goal corresponds to an overarching time period that includes a plurality of epochs (e.g., a week). The epoch goals for the individual epochs within the era may be determined by dividing the era goal by the number of epochs in the era, or the epoch goals may be different from each other. The initial usage goals may be determined based on preset system settings, caregiver input, input from the subject, and/or other parameters. In one embodiment, the one or more initial usage goals are determined by a goal module that is the same as or similar to goal module 42 (shown in FIG. 1 and described above).

At an operation 58, usage by the subject is monitored for a current epoch and/or a current era. This may include determining an amount of time for which the subject receives the pressurized flow of breathable gas to his airway during the current epoch and/or the current era. In one embodiment, operation 58 is performed by a usage module that is the same as or similar to usage module 38.

At an operation 60, usage of the subject is characterized with respect to one or more usage goals. Characterizing the usage of the subject with respect to the usage goals includes comparing the initial epoch and/or era goals determined at operation 56 with the usage monitored at operation 60 to determine whether the user has met or exceeded the initial epoch and/or era goals. In one embodiment, operation 60 is performed by a compliance module that is the same as or similar to compliance module 40 (shown in FIG. 1 and described above).

At an operation 62, feedback information is provided to the subject that is related to the usage of the subject. The feedback information is provided to the subject in a usage report that is transmitted through a communication network to a client device associated with the subject. The feedback information included in the usage report may include usage information, characterization of the subject's usage with the goals (e.g., as determined at operation 60), motivational messages, virtual goods, tips to enhance usage, and/or other information. Generation and/or transmission of a usage report at operation 62 may be performed at the expiration of a periodic interval, based on a therapy event (e.g., end of a session or group of sessions), responsive to receipt of a request from the subject, and/or based on the occurrence of other events. The information included in the usage report, the communication media used to communicate the usage report to the subject, the impetus for the generation and/or transmission of the usage report, and/or other aspects of the usage report may be determined based on use configurable settings. In one embodiment, operation 64 is performed by a feedback module that is the same as or similar to feedback module 44 (shown in FIG. 1 and described above).

At an operation 64, a determination is made as to whether an initial period of time during which the initial usage goal(s) determined at operation 56 are used has expired. The initial period of time may include a fixed period of time (e.g., a predetermined number of epochs and/or eras), or the initial period of time may be a dynamic period of time that enables a clear pattern of usage by the subject to be determined. If the initial period of time is dynamic, then operation 66 includes determining whether a clear pattern of usage can be determined. If the initial period of time is static, then the amount of time that the initial usage goals have been used to monitor compliance is compared with the static period of time. In one embodiment, operation 64 is performed by a processor that is the same as or similar to processor 20 (shown in FIG. 1 and described above). The determination made at operation 64 may be made by the processor in an entirely automated manner, or may be subject to outside inputs (e.g., from a caregiver and/or the subject).

If it is determined at operation 64 that the initial period time has not expired, then method 54 returns back to 58. If it is determined at operation 64 that the initial period of time has expired, then method 54 proceeds to an operation 66. At operation 68, one or more new usage goal(s) are determined. The determination of new usage goal(s) at operation 66 may be dynamic and adaptive based on previous usage by the subject. The determination of usage goal(s) dynamically at operation 66 is designed to provide the subject with realistic usage goals that continually coax the subject toward enhanced usage. By way of non-limiting example, at operation 66 the new usage goal(s) may include a new epoch goal and new era goal. The new epoch goal may be an increase of some amount over per epoch usage of the subject during the initial period of time. Similarly, the new era goal may be an increase of some amount over per era usage during the initial period of time. For instance, per epoch and/or per era usage during the initial period of time may be increased by about 10%, about 20%, about 30%, some amount between about 10% and about 30%, and/or by some other predetermined amount. It will be appreciated that techniques other than a percent increase may be implemented without departing from the scope of this disclosure. In one embodiment, operation 68 is performed by a goal module that is the same as or similar to goal module 42 (shown in FIG. 1 and described above).

In one embodiment, method 54 does not include an initial period. In this embodiment, method 54 begins at operation 66 and usage goals are determined based on caregiver settings, based on predetermined, generic goals, or otherwise determined without taking into account past usage by the subject.

At an operation 68, at least one of the one or more usage goals determined at operation 66 are presented to the subject. The usage goal(s) presented to the subject include a current epoch goal corresponding to the current or upcoming epoch, and/or a current era goal corresponding to the current or upcoming era. In one embodiment, the new usage goal(s) are presented to the subject in the usage report transmitted to the subject at operation 62. In one embodiment, operation 68 is performed by a goal module and feedback module that are similar to or the same as goal module 42 and feedback module 44 (shown in FIG. 1 and described above).

At an operation 70, usage by the subject is monitored for a current epoch and/or a current era. This may include determining an amount of time for which the subject receives the pressurized flow of breathable gas to his airway during the current epoch and/or the current era. In one embodiment, operation 70 is performed by a usage module that is the same as or similar to usage module 38 (shown in FIG. 1 and described above).

At an operation 72, usage of the subject is characterized with respect to one or more usage goals. Characterizing the usage of the subject with respect to the usage goals includes comparing the epoch and/or era goals determined at operation 66 with the usage monitored at operation 70 to determine whether the user has met or exceeded the initial epoch and/or era goals. In one embodiment, operation 72 is performed by a compliance module that is the same as or similar to compliance module 40 (shown in FIG. 1 and described above).

At an operation 74, feedback information is provided to the subject that is related to the usage of the subject. The feedback information is provided to the subject in a usage report that is transmitted through a communication network to a client device associated with the subject. The feedback information included in the usage report may include usage information, characterization of the subject's usage with the goals (e.g., as determined at operation 72), motivational messages, virtual goods, tips to enhance usage, and/or other information. Generation and/or transmission of a usage report at operation 74 may be performed at the expiration of a periodic interval, based on a therapy event (e.g., end of a session or group of sessions), responsive to receipt of a request from the subject, and/or based on the occurrence of other events. The information included in the usage report, the communication media used to communicate the usage report to the subject, the impetus for the generation and/or transmission of the usage report, and/or other aspects of the usage report may be determined based on use configurable settings. In one embodiment, operation 74 is performed by a feedback module that is the same as or similar to feedback module 44 (shown in FIG. 1 and described above).

At an operation 76, a determination is made as to whether one or more usage goals need to be adjusted. Usage goals may be set for adjustment at predetermined intervals. By way of example, in one embodiment, eras are fixed periods of time (rather than rolling windows), and era and epoch goals are adjusted each era based on usage during the previous era. In this embodiment, at the end of an epoch within an era, operation 76 includes determining whether compliance by the subject has exceeded or fallen short of epoch and/or era goals to a degree that adjustment is warranted. For instance, if the subject reaches or exceeds an era goal corresponding to a week in just 5 or 6 nights, it may be determined at operation 76 that the era goal should be adjusted and/or a new era can be started or initialized. Similarly, if the usage of the subject has fallen well below the epoch goal on a nightly basis, and/or if the usage of the subject is well below the era goal for the current era, it may be determined at operation 76 that the epoch and/or era goals need to be adjusted to provide more realistic guidance to the subject. As another example, in one embodiment, an epoch goal is adjusted each epoch based on previous usage (e.g., during a current era that is a rolling window in time). In one embodiment, operation 76 is performed by a goal module that is the same as or similar to goal module 42 (shown in FIG. 1 and described above).

If it is determined at operation 76 that the usage goal(s) do not need to be adjusted, method 54 may proceed back to operation 68 using the current usage goal(s) to monitor further compliance. If it is determined at operation 76 that at least one of the usage goal(s) does need to be adjusted, method 54 proceeds back to operation 66 and the usage goal(s) are adjusted based on past usage. For example, at operation 66, the usage goal(s) may be adjusted based on past usage in the manner described above with respect to operation 66.

Details included herein are for the purpose of illustration based on what is currently considered to be the most practical and preferred embodiments, it is to be understood that such detail is solely for that purpose and that the scope of this specification is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment; wherein the compliance module is configured such that the characterization of the usage of the pressure support device by the subject with respect to the predetermined usage goal includes a representation of the amount of usage of the pressure support device by the subject relative to a goal amount of usage of the predetermined usage goal.

The invention claimed is:

1. A system configured to provide feedback to a subject regarding compliance to a respiratory therapy regimen, the system comprising:
one or more hardware processors configured by machine-readable instructions to:
monitor usage of a pressure support device configured to deliver a pressurized flow of breathable gas to the airway of the subject in accordance with the therapy regimen,
wherein usage of the pressure support device by the subject includes receiving the pressurized flow of breathable gas into the airway,
wherein usage of the pressure support device is monitored during individual epochs of time and during an era of time, the era of time comprising two or more of the individual epochs of time, and
wherein monitoring usage of the pressure support device during the era of time comprises determining a weighted aggregation of usage during the two or more individual epochs of time in the era such that usage during a most recent epoch of time is weighted more heavily than usage during other epochs of time in the determination; and
provide to the subject feedback information related to the usage of the pressure support device by the subject, wherein the providing comprises transmitting the feedback information to a client device associated with the subject through a communication network.

2. The system of claim 1, further comprising:
the pressure support device, which is configured to generate the pressurized flow of breathable gas for delivery to the airway of the subject; and
one or more sensors configured to generate output signals that indicate whether the pressurized flow of breathable gas is being received into the airway of the subject;
wherein the one or more hardware processors are configured to monitor usage of the pressure support device based on the output signals.

3. The system of claim 1, further comprising a server located remotely from the pressure support device, and wherein the one or more hardware processors are configured to monitor usage of the pressure support device based on usage information transmitted to the server from the pressure support device.

4. The system of claim 1, wherein the one or more hardware processors are further configured to characterize the usage of the pressure support device by the subject with respect to a predetermined usage goal, and wherein the feedback information comprises an indication of the characterization of the usage of the pressure support device made by the one or more hardware processors.

5. The system of claim 1, wherein the one or more hardware processors are configured to transmit the feedback information to the client device associated with the subject via one or more of email, short message service message, multimedia messaging service, or TCP/IP communication.

6. A method of providing feedback to a subject regarding compliance to a respiratory therapy regimen, the method comprising:
monitoring usage of a pressure support device configured to deliver a pressurized flow of breathable gas to the airway of the subject in accordance with the therapy regimen,
wherein usage of the pressure support device by the subject includes receiving the pressurized flow of breathable gas into the airway,
wherein usage of the pressure support device is monitored during individual epochs of time and during an era of time, the era of time comprising two or more of the individual epochs of time, and
wherein monitoring usage of the pressure support device during the era of time comprises determining a weighted aggregation of usage during the two or more individual epochs of time in the era such that usage during a most recent epoch of time is weighted more heavily than usage during other epochs of time in the determination; and
transmitting through a communication network to a client device associated with the subject, feedback information related to usage of the pressure support device by the subject.

7. The method of claim 6, further comprising generating the pressurized flow of breathable gas for delivery to the airway of the subject during usage of the pressure support device.

8. The method of claim 6, further comprising receiving usage information transmitted over a communication network from the pressure support device, and wherein monitoring usage is performed based on the received usage information.

9. The method of claim 6, further comprising characterizing the usage of the pressure support device by the subject with respect to a predetermined usage goal, and wherein the feedback information comprises an indication of the characterization of the usage of the pressure support device.

10. The method of claim 6, wherein transmitting the feedback information to the client device associated with the subject is performed via one or more of email, short message service message, multimedia messaging service, or TCP/IP communication.

11. A system for providing feedback to a subject regarding compliance to a respiratory therapy regimen, the system comprising:
 means for monitoring usage of a pressure support device configured to deliver a pressurized flow of breathable gas to the airway of the subject in accordance with the therapy regimen,
  wherein usage of the pressure support device by the subject includes receiving the pressurized flow of breathable gas into the airway,
  wherein usage of the pressure support device is monitored during individual epochs of time and during an era of time, the era of time comprising two or more of the individual epochs of time, and
  wherein monitoring usage of the pressure support device during the era of time comprises determining a weighted aggregation of usage during the two or more individual epochs of time in the era such that usage during a most recent epoch of time is weighted more heavily than usage during other epochs of time in the determination; and
 means for transmitting, through a communication network to a client device associated with the subject, feedback information related to usage of the pressure support device by the subject.

12. The system of claim 11, further comprising means for generating the pressurized flow of breathable gas for delivery to the airway of the subject during usage of the pressure support device.

13. The system of claim 11, further comprising means for receiving usage information transmitted over a communication network from the pressure support device, and wherein the means for monitoring usage is configured to monitor usage based on the received usage information.

14. The system of claim 11, further comprising means for characterizing the usage of the pressure support device by the subject with respect to the a predetermined usage goal, and wherein the feedback information comprises an indication of the characterization of the usage of the pressure support device.

15. The system of claim 11, wherein the means for transmitting the feedback information to the client device associated with the subject is configured to transmit the feedback information via one or more of email, short message service message, multimedia messaging service, or TCP/IP communication.

* * * * *